(12) United States Patent
Zhang et al.

(10) Patent No.: US 10,336,699 B2
(45) Date of Patent: Jul. 2, 2019

(54) METHOD FOR SYNTHESIZING N,N'-BIS(2,2,6,6-TETRAMETHYL-4-PIPERIDYL)-1,3-BENZENEDICARBOXAMIDE

(71) Applicant: SUNSHOW (YANTAI) SPECIALTY CHEMICAL COMPANY LIMITED, Yantai (CN)

(72) Inventors: Xiuxiu Zhang, Yantai (CN); Xuqiao Gai, Yantai (CN)

(73) Assignee: SUNSHOW (YANTAI) SPECIALTY CHEMICAL COMPANY LIMITED, Yantai (CN)

( * ) Notice: Subject to any disclaimer, the term of this patent is extended or adjusted under 35 U.S.C. 154(b) by 0 days.

(21) Appl. No.: 15/727,616

(22) Filed: Oct. 8, 2017

(65) Prior Publication Data
US 2019/0040011 A1 Feb. 7, 2019

(30) Foreign Application Priority Data
Aug. 2, 2017 (CN) .......................... 2017 1 0652766

(51) Int. Cl.
*C07D 211/58* (2006.01)
*B01J 37/02* (2006.01)
*B01J 29/03* (2006.01)

(52) U.S. Cl.
CPC ......... *C07D 211/58* (2013.01); *B01J 37/0207* (2013.01); *B01J 29/03* (2013.01)

(58) Field of Classification Search
CPC ...... C07D 211/58; B01J 37/0207; B01J 29/03
See application file for complete search history.

(56) References Cited

U.S. PATENT DOCUMENTS

2006/0199963 A1 9/2006 Mehrer

FOREIGN PATENT DOCUMENTS

| CN | 103508938 A | | 1/2014 |
| CN | 103554009 A | | 2/2014 |
| CN | 106905225 | * | 2/2017 |
| WO | 1997043335 A1 | | 11/1997 |
| WO | 2017024608 | * | 2/2016 |

* cited by examiner

Primary Examiner — D Margaret M Seaman
(74) Attorney, Agent, or Firm — W&K IP

(57) ABSTRACT

The present invention relates to a method for synthesizing N,N'-bis(2,2,6,6-tetramethyl-4-piperidyl)-1,3-benzenedicarboxamide as shown in the following formula (III),

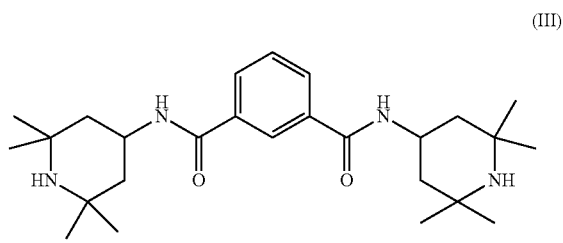

(III)

comprising the following steps that a compound of the following formula (I) and a compound of the following formula (II) react under stirring in an organic solvent in the presence of a solid supported catalyst, and after the completion of the reaction, a compound of the formula (III) is obtained by post-treatment,

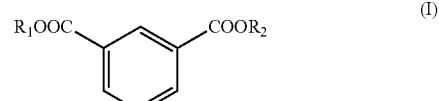

(I)

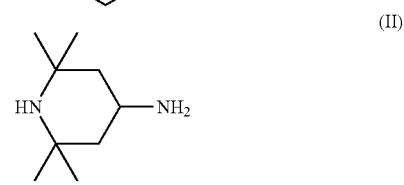

(II)

wherein R1 to R2 are each the same or different selected from $C_{1-6}$ alkyl. The method can achieve good technical effects through the use of a unique catalyst and the compounding of the organic solvent, has the advantages of reduced pollution, good environment and significant improvement on yield compared with the prior art, can provide more inexpensive functional additives for the field of plastic processing, and has good industrial production prospects and application potential.

5 Claims, 2 Drawing Sheets

METHOD FOR SYNTHESIZING N,N'-BIS(2,2,6,6-TETRAMETHYL-4-PIPERIDYL)-1,3-BENZENEDICARBOXAMIDE

CROSS-REFERENCE TO RELATED APPLICATIONS

This application claims priority to Chinese Patent Application No. 201710652766.1 with a filing date of Aug. 2, 2017. The content of the aforementioned application, including any intervening amendments thereto, are incorporated herein by reference.

TECHNICAL FIELD

The present invention relates to a synthetic method of plastic additives, and more particularly relates to a method for synthesizing N,N'-bis (2,2,6,6-tetramethyl-4-piperidyl)-1,3-benzenedicarboxamide, belonging to the technical field of organic synthesis.

RELATED ART

Nylon (PA) is a crystalline thermoplastic engineering plastic with high tensile strength, good wear resistance and many other excellent performance, and is widely applied to industry and agriculture because of the excellent performance.

However, on the other hand, since an amide group (—NHCO—) contained in a nylon structure belongs to a chromophore group, and it has stronger polarity and is susceptible to environmental factors such as heat, oxygen, ultraviolet rays, moisture and the like, so that a series of pyrolysis reactions can be carried out to generate water, $CO_2$, CO, hydrocarbons and a small amount of cyclopentanone, etc.; with its reactions, a main chain of a polymer is cut off, and then the reduction in relative molecular mass, the reduction in various performance, color change and many other defects are caused.

In order to overcome these defects, it is necessary to increase the weatherability, stability and other performance of the nylon by adding a light stabilizer, an antioxidant and other additives in nylon polymerization, nylon spinning or modified products, the appearance and color of a nylon product after being used for a long time are kept as much as possible, and the service life is prolonged.

For this objective, a lot of in-depth studies are carried out on a nylon stabilizer by researchers to obtain an excellent-performance hindered amine stabilizer, i.e. N,N'-bis(2,2,6,6-tetra Methyl-4-piperidinyl)-1,3-benzenedicarboxamide by synthesis, and its structural formula is as follows:

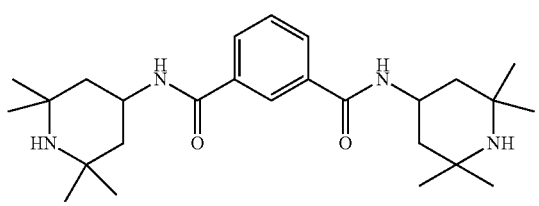

The compound can significantly improve various performance of nylon polymers, such as thermal stability, light stability, chemical stability, fuel affinity, weatherability, thereby greatly improving the stability of nylon products, and significantly prolonging the service life; the compound is known as a "multi-functional additive" in plastic industry, and is widely applied to plastics, textiles, chemical fibers, and many other fields.

It is also because of its excellent performance, a number of studies have been carried out on its synthetic methods so as to obtain various preparation methods, and a following preparation method with the same reaction path is disclosed in the prior art such as CN103508938A, WO9743335A, U.S. 20060199963, WO2004016591 and CN103554009A:

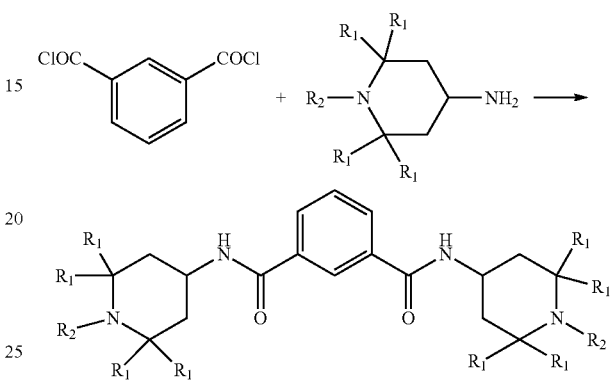

wherein R1 to R2 are each independently H or lower alkyl.

In these methods, m-phthaloyl chloride is used as a raw material, so that subsequent treatment is extremely complicated, a lot of waste water is generated, and the environmental pollution is very serious, therefore, the industrial production cannot be achieved, or the industrial production can be achieved, but the cost of production is high, the pollution prevention and control is difficult, and thus enough competitiveness is difficult to obtain.

In order to overcome the defects of acyl chloride in use, improvement on its synthesis is made, for example, dialkyl phthalate is used to replace the m-phthaloyl chloride in a prior application CN104974075A of the applicant, thereby greatly reducing the difficulty of subsequent treatment and environmental pollution, and achieving good technical effects, but the yield is only about 90%, and so there is still room for improvement.

As mentioned above, the current methods for synthesizing the N,N'-bis(2,2,6,6-tetramethyl-4-piperidyl)-1,3-benzenedicarboxamide all have some defects, and there is still need and demand for further research on how to use to overcome these defects, such as serious pollution, the use of the acyl chloride and lower yield, which not only have very important significance and economic value in industrial production, but also is the current research hotspot and emphasis in the field, and is the basis and power of the completion of the present invention.

SUMMARY

As described above, in order to explore a novel method for synthesizing N,N'-bis(2,2,6,6-tetramethyl-4-piperidyl)-1,3-benzenedicarboxamide, the present inventor conducted in-depth research to complete the present invention after paying a lot of creative work.

Specifically, in a first aspect, the present invention relates to a method (III)

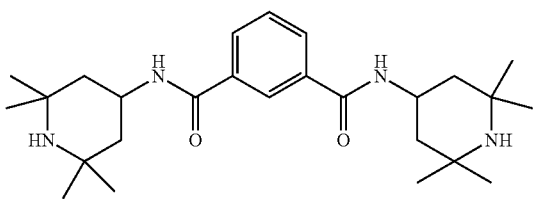

for synthesizing the N,N'-bis(2,2,6,6-tetramethyl-4-piperidyl)-1,3-benzenedicarboxamide as shown in the following formula (III), comprising the following specific steps that a compound of the following formula (I) and a compound of the following formula (II) react under stirring in an organic solvent in the presence of a solid supported catalyst, and after the completion of the reaction, a compound of the formula (III) is obtained by post-treatment, wherein R1 to R2 are each the same or differently selected from $C_{1-6}$ alkyl.

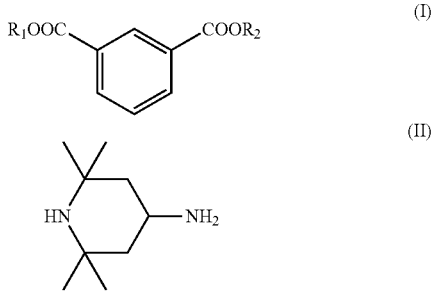

In the synthetic method of the present invention, the C1-C6 alkyl refers to a straight chain or branched alkyl having 1 to 6 carbon atoms, and is not limited to, for example, methyl, ethyl, n-propyl, isopropyl, n-butyl, sec-butyl, isobutyl, tert-butyl, n-pentyl, isopentyl or n-hexyl, etc.

For example, the compound of the formula (I) may be dimethyl isophthalate, diethyl isophthalate, di-n-propyl isophthalate, diisopropyl isophthalate, di-n-butyl isophthalate, diisobutyl isophthalate, di-tert-butyl isophthalate, di-n-pentyl isophthalate, diisopentyl isophthalate or di-n-hexyl isophthalate.

In the synthetic method of the present invention, the solid supported catalyst is prepared by a method comprising the following steps:

S1: treating a KIT-1 molecular sieve with 120° C. to 130° C. water vapor for 20 to 30 minutes, then naturally cooling to room temperature and thoroughly drying in vacuum to obtain a heat-treated molecular sieve;

S2: immersing the heat-treated molecular sieve in a nitric acid aqueous solution with a molar concentration of 0.5 to 0.7 mol/L for 2 to 3 hours and then thoroughly washing with deionized water and completely drying to obtain an acid-treated molecular sieve;

S3: preparing a nickel chloride aqueous solution with a molar concentration of 1.0 mol/L and a lanthanum trifluoromethanesulfonate aqueous solution with a molar concentration of 0.4 mol/L respectively;

S4: impregnating the acid-treated molecular sieve with the nickel chloride aqueous solution, enabling the mass ratio of adsorbed nickel ions to the heat-treated molecular sieve of Step 1 to be (0.05 to 0.08) to 1, and then completely drying to obtain a nickel ion supported molecular sieve; and S5: impregnating the nickel ion supported molecular sieve with the lanthanum trifluoromethanesulfonate aqueous solution until the molar ratio of adsorbed lanthanum ions to the adsorbed nickel ions in step S4 is (1.5 to 2.5) to 1, and then completely drying again to obtain the solid supported catalyst.

Further, in step S1, the KIT-1 molecular sieve is a well-known class of molecular sieve which can be purchased through a variety of commercial channels and will not be described in detail herein.

Further, in step S1, the water vapor treatment means that the KIT-1 molecular sieve is subjected to high-temperature water vapor treatment in a 120° C. to 130° C. water vapor air stream for 20 to 30 minutes to complete the heat treatment.

Further, in step S4, the mass ratio of the adsorbed nickel ions to the heat-treated molecular sieve obtained in step S1 is (0.05 to 0.08) to 1, and may be, for example, 0.05 to 1, 0.06 to 1, 0.07 to 1 or 0.08 to 1.

Further, in step S5, the molar ratio of the adsorbed lanthanum ions to the adsorbed nickel ions in step S4 is (1.5 to 2.5) to 1, and may be, for example, 1.5 to 1, 2 to 1 or 2.5 to 1, most preferably 2 to 1; it is found by the inventor that when the molar ratio is 2 to 1, the best technical effects can be achieved, and the nickel ions and the lanthanum ions may achieve the most uniform and the most appropriate adsorption amount and metal ion distribution in pores of the molecular sieve, so that the best technical effects can be achieved, and a follow-up in-depth study will be conducted by the inventor in the next step.

In the synthetic method of the present invention, the organic solvent is any one or a mixture of multiple of toluene, benzene, N,N-dimethylformamide (DMF), chlorobenzene, acetonitrile, N-methylpyrrolidone (NMP) or polyethylene glycol 200 (PEG-200), most preferably a mixture of the acetonitrile and the polyethylene glycol 200 (PEG-200) with volume ratio of 3:1.

Further, the amount of the organic solvent is not strictly limited, and it will be apparent to those skilled in the art that appropriate selection and determination can be made according to actual situations, for example, the amount of the organic solvent should facilitate the reaction and the post-treatment, which will not be described in detail herein.

In the synthetic method of the present invention, the molar ratio of the compound of the formula (I) to the compound of the formula (II) is 1 to (0.5 to 0.8), and may be, for example, 1 to 0.5, 1 to 0.6, 1 to 0.7 or 1 to 0.8.

In the synthetic method of the present invention, the molar ratio of the compound of the formula (I) to the nickel ions in the solid supported catalyst is 1 to (0.08 to 0.14), and may be, for example, 1 to 0.08, 1 to 0.1, 1 to 0.12 or 1 to 0.14; that is, the amount of the solid supported catalyst is as follows: the molar ratio of the compound of the formula (I) to the nickel ions is 1 to (0.08 to 0.14), and may be, for example, 1 to 0.08, 1 to 0.1, 1 to 0.12 or 1 to 0.14, calculated by the supported nickel ions.

In the synthetic method of the present invention, the reaction temperature is 60° C. to 80° C., and may be, for example, 60° C., 70° C. or 80° C.

In the synthetic method of the present invention, the reaction time is 12 to 17 hours, and may be, for example, 12 hours, 13 hours, 14 hours, 15 hours, 16 hours or 17 hours.

In the synthetic method of the present invention, the post-treatment after the completion of the reaction is the same as that of the applicant's prior application CN104974075A, will not be described in detail herein, and specifically refers to the prior application.

In a second aspect, the present invention also relates to the above-mentioned solid supported catalyst.

The present inventor has found that the solid supported catalyst obtained by the above-mentioned treatment can not only obtain a desired product (i.e., the N,N'-bis(2,2,6,6-tetramethyl-4-piperidinyl)-1,3-benzenedicarboxamide) with a good yield, but also has excellent cycling stability, and has a very high product yield after being repeatedly used for 30 times, exhibiting excellent cycling stability and reactivity.

As described above, the present invention provides the method for synthesizing the plastic additive, the N,N'-bis(2,2,6,6-tetramethyl-4-piperidyl)-1,3-benzenedicarboxamide, and the method can achieve good technical effects through the use of a novel catalyst and the compounding of the organic solvent, has many advantages of reduced pollution, good environment (due to the absence of an acyl chloride compound) and significant improvement on yield compared with the prior art, can provide more inexpensive functional additives for the field of plastic processing, and has good industrial production prospects and application potential.

DETAILED DESCRIPTION

Figure 1:
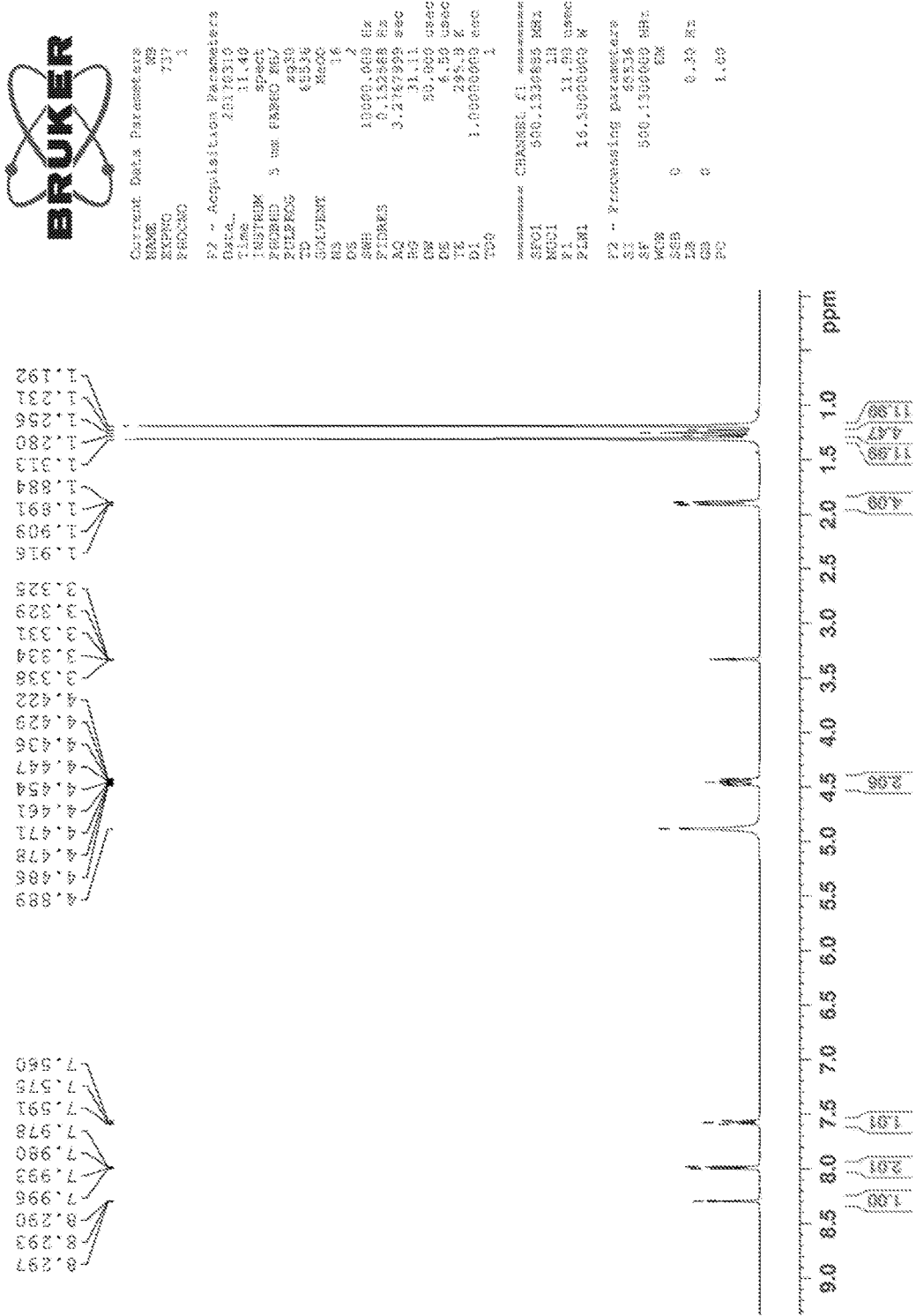
FIG. 1 is a nuclear magnetic resonance hydrogen spectrum of N,N'-bis(2,2,6,6-tetramethyl-4-piperidyl)-1,3-benzenedicarboxamide obtained in Example 1 of the present invention.

The present invention will be described in detail by way of specific examples, but the uses and objects of these exemplary embodiments are merely illustration of the present invention and are not to be construed as limiting the actual protection scope of the present invention in any way, and to which the scope of protection of the present invention is not limited.

Preparation of Solid Supported Catalysts

Preparation Example 1: Preparation of Catalyst C1

S1: treating a KIT-1 molecular sieve with 125° C. water vapor for 25 minutes, then naturally cooling to room temperature and thoroughly drying in vacuum to obtain a heat-treated molecular sieve;

S2: immersing the heat-treated molecular sieve in a nitric acid aqueous solution with a molar concentration of 0.6 mol/L for 2.5 hours and then thoroughly washing with deionized water and completely drying to obtain an acid-treated molecular sieve;

S3: preparing a nickel chloride aqueous solution with a molar concentration of 1.0 mol/L and a lanthanum trifluoromethanesulfonate aqueous solution with a molar concentration of 0.4 mol/L respectively;

S4: impregnating the acid-treated molecular sieve with the nickel chloride aqueous solution, enabling the mass ratio of adsorbed nickel ions to the heat-treated molecular sieve of Step 1 to be 0.065 to 1, and then thoroughly washing with the deionized water and completely drying again to obtain a nickel ion supported molecular sieve; and S5: impregnating the nickel ion supported molecular sieve with the lanthanum trifluoromethanesulfonate aqueous solution until the molar ratio of adsorbed lanthanum ions to the adsorbed nickel ions in step S4 is 2 to 1, and then thoroughly washing with the deionized water and completely drying again to obtain a solid supported catalyst named C1.

Preparation Example 2: Preparation of Catalyst C2

S1: treating a KIT-1 molecular sieve with 120° C. water vapor for 30 minutes, then naturally cooling to room temperature and thoroughly drying in vacuum to obtain a heat-treated molecular sieve;

S2: immersing the heat-treated molecular sieve in a nitric acid aqueous solution with a molar concentration of 0.5 mol/L for 3 hours and then thoroughly washing with deionized water and completely drying to obtain an acid-treated molecular sieve;

S3: preparing a nickel chloride aqueous solution with a molar concentration of 1.0 mol/L and a lanthanum trifluoromethanesulfonate aqueous solution with a molar concentration of 0.4 mol/L respectively;

S4: impregnating the acid-treated molecular sieve with the nickel chloride aqueous solution, enabling the mass ratio of adsorbed nickel ions to the heat-treated molecular sieve of Step 1 to be 0.05 to 1, and then thoroughly washing with the deionized water and completely drying again to obtain a nickel ion supported molecular sieve; and S5: impregnating the nickel ion supported molecular sieve with the lanthanum trifluoromethanesulfonate aqueous solution until the molar ratio of adsorbed lanthanum ions to the adsorbed nickel ions in step S4 is 2 to 1, and then thoroughly washing with the deionized water and completely drying again to obtain a solid supported catalyst named C2.

Preparation Example 3: Preparation of Catalyst C3

S1: treating a KIT-1 molecular sieve with 130° C. water vapor for 20 minutes, then naturally cooling to room temperature and thoroughly drying in vacuum to obtain a heat-treated molecular sieve;

S2: immersing the heat-treated molecular sieve in a nitric acid aqueous solution with a molar concentration of 0.7 mol/L for 2 hours and then thoroughly washing with deionized water and completely drying to obtain an acid-treated molecular sieve;

S3: preparing a nickel chloride aqueous solution with a molar concentration of 1.0 mol/L and a lanthanum trifluoromethanesulfonate aqueous solution with a molar concentration of 0.4 mol/L respectively;

S4: impregnating the acid-treated molecular sieve with the nickel chloride aqueous solution, enabling the mass ratio of adsorbed nickel ions to the heat-treated molecular sieve of Step 1 to be 0.08 to 1, and then thoroughly washing with the deionized water and completely drying again to obtain a nickel ion supported molecular sieve; and S5: impregnating the nickel ion supported molecular sieve with the lanthanum trifluoromethanesulfonate aqueous solution until the molar ratio of adsorbed lanthanum ions to the adsorbed nickel ions in step S4 is 2 to 1, and then thoroughly washing with the deionized water and completely drying again to obtain a solid supported catalyst named C3.

Comparative Preparation Examples 1-3: Preparation of Catalysts D1-D3

Comparative Preparation Example 1: other operations were the same except that step S1 was omitted, so that the Preparation Example 1 was repeated to obtain a catalyst named D1 (i.e., the KIT-1 molecular sieve was directly subjected to the acid treatment in Step S2 without performing the water vapor heat treatment in step S1).

Comparative Preparation Example 2: other operations were the same except that step S2 was omitted, so that the Preparation Example 2 was repeated to obtain a catalyst named D2 (i.e., the KIT-1 molecular sieve was subjected to the water vapor heat treatment in Step S1 only and then directly subjected to steps S3-S5 without performing the acid treatment in step S2).

Comparative Preparation Example 3: other operations were the same except that steps S1-S2 were omitted, so that the Preparation Example 3 was repeated to obtain a catalyst named D3 (i.e., the KIT-1 molecular sieve was directly subjected to steps S3-S5 without performing the water vapor heat treatment and the acid treatment in steps S1-S2).

Comparative Preparation Examples 4-9: Preparation of Catalysts D4-D9

Comparative Preparation Examples 4-6: other operations were not changed except that step S5 was omitted, so that the Preparation Examples 1-3 were respectively repeated, and thus Comparative Preparation Examples 4-6 were obtained in sequence (that is, only steps S1-S4 were performed without impregnating with the lanthanum trifluoromethanesulfonate aqueous solution), and resulting catalysts were named D4, D5 and D6.

Comparative Preparation Examples 7-9: other operations were not changed except that step S4 was omitted, so that the Preparation Examples 1-3 were respectively repeated, and thus Comparative Preparation Examples 7-9 were obtained in sequence (that is, only steps S1-S3 and S5 were performed without impregnating with the nickel chloride aqueous solution, and the amount of adsorbed lanthanum ions was the same as that in the corresponding Preparation Examples 1 to 3 respectively), and resulting catalysts were named D7, D8 and D9.

Comparative Preparation Examples 10-15: Preparation of Catalysts D10-D15

Other operations were not changed except that the molar ratio of the adsorbed lanthanum ions in step S5 to the adsorbed nickel ions in step S4 was the same as that in a table below, so that Comparative Preparation Examples 10-15 were repeated in the same manner as in Preparation Examples 1-3 to obtain catalysts D10-D15 in sequence, wherein the mass ratio of the two, corresponding Preparation Examples and catalyst names were shown in the table below:

| Numbers | Molar Ratio | Corresponding Preparation Example | Obtained Catalyst |
|---|---|---|---|
| Comparative Preparation Example 10 | 1.5 to 1 | Preparation Example 1 | D10 |
| Comparative Preparation Example 11 | 2.5 to 1 | Preparation Example 2 | D11 |
| Comparative Preparation Example 12 | 1.7 to 1 | Preparation Example 3 | D12 |
| Comparative Preparation Example 13 | 2.3 to 1 | Preparation Example 1 | D13 |
| Comparative Preparation Example 14 | 1.9 to 1 | Preparation Example 2 | D14 |
| Comparative Preparation Example 15 | 2.1 to 1 | Preparation Example 3 | D15 |

Further, the post-treatment after the completion of the reaction was carried out according to the applicant's prior application CN104974075A, and will not be described in detail in all of the following Examples and Comparative Examples.

Example 1

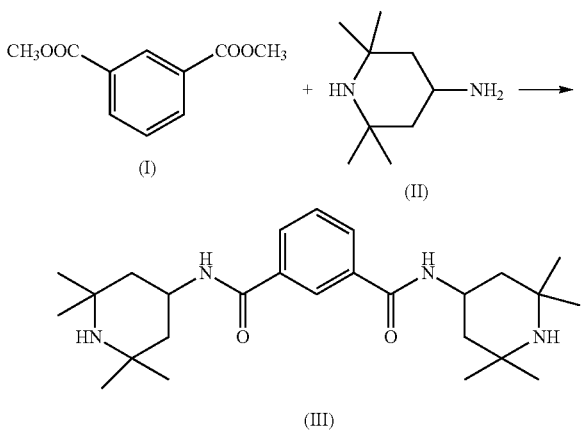

Figure 2:
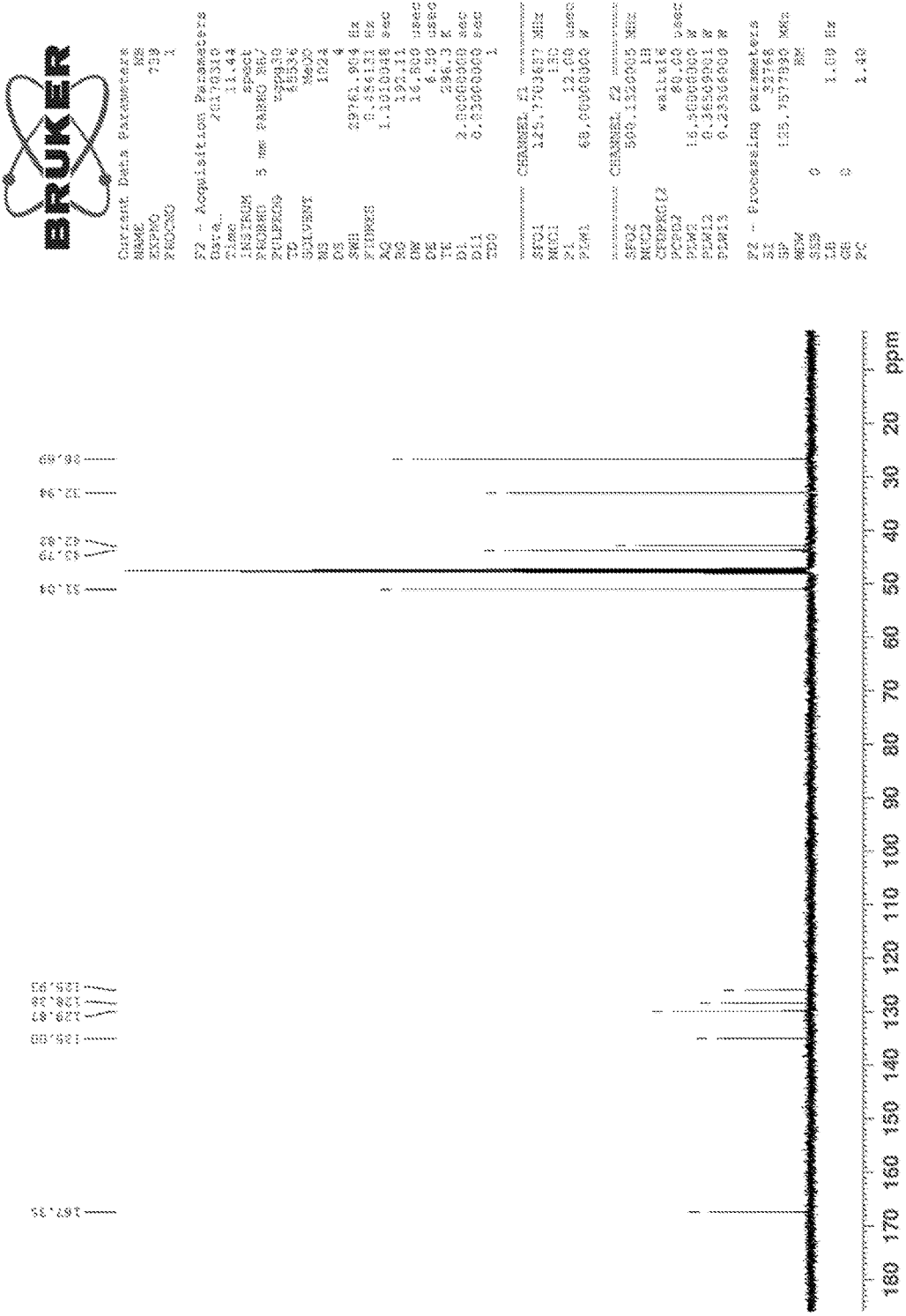
FIG. 2 is a nuclear magnetic resonance carbon spectrum of N,N'-bis(2,2,6,6-tetramethyl-4-piperidyl)-1,3-benzenedicarboxamide obtained in Example 1 of the present invention.

To a suitable amount of an organic solvent (a mixture of acetonitrile and polyethylene glycol 200 (PEG-200) with volume ratio of 3 to 1) was added 100 mmol of a compound of the formula (I), 65 mmol of a compound of the formula (II), a solid supported catalyst C1 (the amount of the C1 was as follows: the molar ratio of the compound of the formula (I) to nickel ions in the C1 was 1 to 0.11) at room temperature, and then the temperature was raised to 70° C., and reaction was continuously carried out for 15 hours under stirring at this temperature;

After the completion of the reaction, a compound of the formula (III) in the form of a white solid was obtained, i.e., N,N'-bis(2,2,6,6-tetramethyl-4-piperidyl)-1,3-benzenedicarboxamide, the yield was 96.7%, and the characterization data was as follows (spectra were shown in FIG. 1 and FIG. 2 respectively):

1HNMR (MeOD, 500 MHz): δ 8.29 (t, J=1.65 Hz, 1H), 7.93-8.03 (dd, J=7.75 Hz, 1.4 Hz, 2H), 7.57 (t, J=7.75 Hz, 1H), 4.4-4.5 (tt, J=3.6 Hz, 12.30 Hz, 2H), 1.85-1.95 (dd, J=3.5 Hz, 12.6 Hz, 4H), 1.31 (m, 12H); 1.22-1.29 (t, J=12.45 Hz, 4H), 1.19 (m, 12H).

13CNMR (MeOD, 500 MHz): 167.35, 135.00, 129.87, 128.38, 125.93, 51.04, 43.79, 42.82, 32.94, 26.69.

Example 2

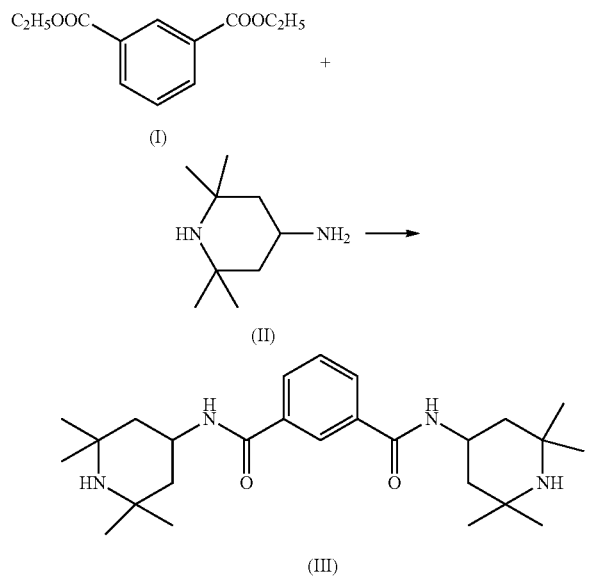

To a suitable amount of an organic solvent (a mixture of acetonitrile and polyethylene glycol 200 (PEG-200) with volume ratio of 3 to 1) was added 100 mmol of a compound of the formula (I), 50 mmol of a compound of the formula (II), a solid supported catalyst C2 (the amount of the C2 was as follows: the molar ratio of the compound of the formula (I) to nickel ions in the C2 was 1 to 0.14) at room temperature, and then the temperature was raised to 60° C., and reaction was continuously carried out for 17 hours under stirring at this temperature;

After the completion of the reaction, a compound of the formula (III) in the form of a white solid was obtained, i.e., N,N'-bis(2,2,6,6-tetramethyl-4-piperidyl)-1,3-benzenedicarboxamide, the yield was 96.3%, and the characterization data was the same as those in Example 1.

Example 3

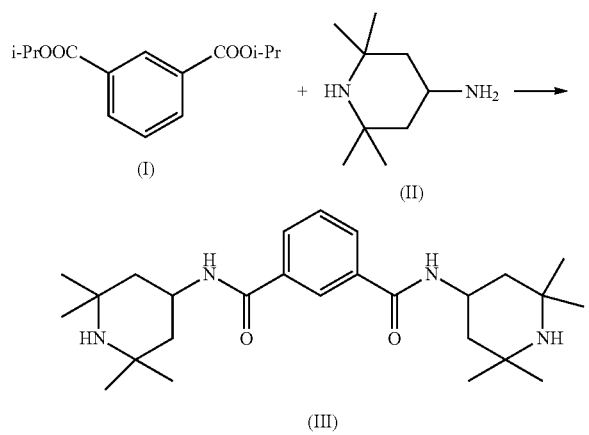

To a suitable amount of an organic solvent (a mixture of acetonitrile and polyethylene glycol 200 (PEG-200) with volume ratio of 3 to 1) was added 100 mmol of a compound of the formula (I) (wherein i-Pr is isopropyl), 80 mmol of a compound of the formula (II), a solid supported catalyst C3 (the amount of the C3 was as follows: the molar ratio of the compound of the formula (I) to nickel ions in the C3 was 1 to 0.08) at room temperature, and then the temperature was raised to 80° C., and the reaction was continuously carried out for 12 hours under stirring at this temperature;

After the completion of the reaction, a compound of the formula (III) in the form of a white solid was obtained, i.e., N,N'-bis(2,2,6,6-tetramethyl-4-piperidyl)-1,3-benzenedicarboxamide, the yield was 96.2%, and the characterization data was the same as those in Example 1.

Comparative Examples 1-3: Investigation of Catalyst Treatment Means

Comparative Example 1: other operations were not changed except that the catalyst C1 was replaced with D1, so that the Example 1 was repeated to obtain a Comparative Example 1.

Comparative Example 2: other operations were not changed except that the catalyst C2 was replaced with D2, so that the Example 1 was repeated to obtain a Comparative Example 2.

Comparative Example 3: other operations were not changed except that the catalyst C3 was replaced with D3, so that the Example 1 was repeated to obtain a Comparative Example 3.

Results were shown in Table 1 below.

TABLE 1

| Numbers | Catalysts | Product Yield(%) |
|---|---|---|
| Comparative Example 1 | D1 | 82.9 |
| Comparative Example 2 | D2 | 87.1 |
| Comparative Example 3 | D3 | 69.5 |

It could be seen that the treatment of the KIT-1 molecular sieve was very important, and the yield was reduced significantly when only the water vapor heat treatment or the acid treatment was carried out; the yield was reduced more significantly when the water vapor heat treatment and the acid treatment were not carried out, proving that the best technical effects could be obtained only when the molecular sieve was subjected to the water vapor heat treatment and the acid treatment at the same time (the pore regularity could be improved by the water vapor heat treatment, and the number of active adsorption points might be increased by the acid treatment).

Comparative Examples 4-9: Investigation of Supported Active Metals

Other operations were not changed except that the catalysts were respectively replaced with the following catalysts, so that the Examples 1-3 were repeated to obtain Comparative Examples 4-9. The used catalysts, corresponding relations of Examples and product yield were shown in Table 2 below.

TABLE 2

| Numbers | Catalysts | Corresponding Examples | Product Yield(%) |
|---|---|---|---|
| Comparative Example 4 | D4 | Example 1 | 62.2 |
| Comparative Example 5 | D5 | Example 2 | 59.4 |
| Comparative Example 6 | D6 | Example 3 | 60.7 |
| Comparative Example 7 | D7 | Example 1 | 87.3 |
| Comparative Example 8 | D8 | Example 2 | 86.9 |
| Comparative Example 9 | D9 | Example 3 | 86.8 |

It could be seen that: 1. when one active metal was supported only, the product yield was reduced significantly; especially when nickel metal was supported only, the product yield was reduced more significantly compared with the product yield that only the lanthanum metal was supported; 2. it could be seen by combining the yield of Examples 1-3 that the yield was improved significantly when the two active metals were supported at the same time, proving that the two metals played an unexpected synergistic promoting effect.

Comparative Examples 10-15: Investigation of Supporting Amounts of Lanthanum and Nickel Metals Example 1 with the highest yield was used as a repeating basis, the catalyst C1 in Example 1 was respectively replaced with the catalysts D10-D15, and other operations were not changed, and the Example 1 was repeated to obtain Comparative Examples 10-15 in sequence.

The used catalysts, the molar ratios of lanthanum to nickel in the catalysts and the final product yield were shown in Table 3 below.

TABLE 3

| Numbers | Catalysts | Molar ratio of Lanthanum to Nickel | Product Yield(%) |
|---|---|---|---|
| Comparative Example 10 | D10 | 1.5 to 1 | 90.4 |
| Comparative Example 11 | D11 | 2.5 to 1 | 91.7 |
| Comparative Example 12 | D12 | 1.7 to 1 | 93.6 |
| Comparative Example 13 | D13 | 2.3 to 1 | 94.5 |
| Comparative Example 14 | D14 | 1.9 to 1 | 94.9 |
| Comparative Example 15 | D15 | 2.1 to 1 | 95.3 |

It could be seen that: 1. the molar ratio of lanthanum to nickel supported in the catalyst had a significant effect on the final product yield, and the best technical effects could be obtained when the molar ratio was 2 to 1; 2. compared with the best molar ratio of 2 to 1, even there was the same deviation value, the yield of higher than 2 to 1 was better than the yield of lower than 2 to 1 (for example, although there was the same deviation value, the yield of D13 was higher than the yield of D12).

Comparative Examples 16-22: Investigation of Organic Solvents

Other operations were not changed except that a mixed organic solvent was replaced with the following single organic solvent, so that Examples 1-3 were repeated to obtain Comparative Examples 16 to 22. The used catalysts, corresponding relations of Examples and product yield were shown in Table 4 below.

TABLE 4

| Numbers | Organic Solvent | Corresponding Examples | Product Yield(%) |
|---|---|---|---|
| Comparative Example 16 | Toluene | Example 1 | 94.8 |
| Comparative Example 17 | Benzene | Example 2 | 93.6 |
| Comparative Example 18 | DMF | Example 3 | 95.1 |
| Comparative Example 19 | Chlorobenzene | Example 1 | 90.4 |
| Comparative Example 20 | Acetonitrile | Example 2 | 92.5 |
| Comparative Example 21 | NMP | Example 3 | 89.7 |
| Comparative Example 22 | PEG-200 | Example 1 | 93.9 |

It could be seen that when a single solvent was used, the yield was lower than that obtained when a mixture of acetonitrile and polyethylene glycol 200 (PEG-200) with volume ratio of 3 to 1 was used, proving that the solvent compounding had a certain effect on the final result.

Investigation of Cycling Stability and Reactivity of Catalysts

After the completion of reaction, the catalyst was filtered out and sufficiently dried, and then the corresponding Examples (reaction conditions were identical) were repeated again so as to investigate the cycling stability and reactivity of the catalyst of the present invention.

More specifically, by taking the Example 1 as an example, after the completion of the first reaction, the catalyst was filtered out and sufficiently dried, the Example 1 was repeated for many times according to the same conditions, and the 10th, 20th and 30th product yield was respectively tested; the specific results were shown in Table 5 below, and the first yield was listed together for a clearer comparison.

TABLE 5

| | Product Yield (%) for Different Cycle Times | | | |
|---|---|---|---|---|
| Numbers | 1 | 10 | 20 | 30 |
| Example 1 | 96.7 | 95.0 | 91.4 | 84.9 |
| Example 2 | 96.3 | 94.2 | 90.5 | 82.7 |
| Example 3 | 96.2 | 94.7 | 90.3 | 82.1 |

It could be seen that the catalyst of the present invention had good cycling stability and reactivity, and had a good yield of more than 80% even after 30 cycles, exhibiting excellent stability, providing a basis for large-scale industrial production, significantly reducing business cost and improving productivity.

As described above, the present invention provides the method for synthesizing the plastic additive, N,N'-bis(2,2,6,6-tetramethyl-4-piperidyl)-1,3-benzenedicarboxamide, and the method can achieve good technical effects through the use of the novel catalyst and the compounding of the organic solvent, has many advantages of reduced pollution, good environment and significant improvement on yield compared with the prior art, can provide more inexpensive functional additives for the field of plastic processing, and has good industrial production prospects and application potential.

It is to be understood that the uses of these examples are for the purpose of illustrating the present invention and are not intended to limit the scope of protection of the present invention. In addition, it is also to be understood that various changes, modifications and/or variations of the present invention can be made by those skilled in the art after reading the technical content of the present invention, and all these equivalents also fall within the scope of protection limited by the appended claims of the application.

We claim:

1. A method for synthesizing N,N'-bis(2,2,6,6-tetramethyl-4-piperidyl)-1,3-benzenedicarboxamide as shown in the following formula (III),

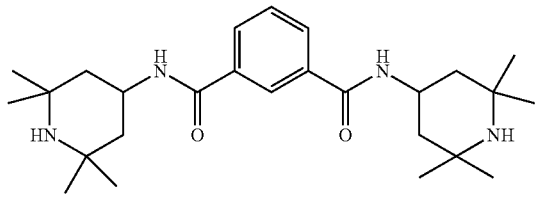

(III)

comprising the following specific steps that a compound of the following formula (I) and a compound of the following formula (II) react under stirring in an organic solvent in the presence of a solid supported catalyst, and after the completion of the reaction, a compound of the formula (III) is obtained by post-treatment,

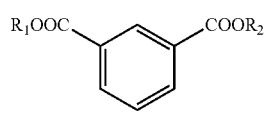

(I)

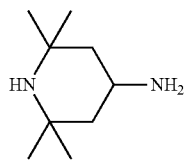

(II)

wherein R1 and R2 are each the same or differently selected from $C_{1-6}$ alkyl; and wherein, the solid supported catalyst is prepared by a method comprising the following steps:

S1: treating a KIT-1 molecular sieve with 120° C. to 130° C. water vapor for 20 to 30 minutes, then naturally cooling to room temperature and thoroughly drying in vacuum to obtain a heat-treated molecular sieve;

S2: immersing the heat-treated molecular sieve in a nitric acid aqueous solution with a molar concentration of 0.5 to 0.7 mol/L for 2 to 3 hours and then thoroughly washing with deionized water and completely drying to obtain an acid-treated molecular sieve;

S3: preparing a nickel chloride aqueous solution with a molar concentration of 1.0 mol/L and a lanthanum trifluoromethanesulfonate aqueous solution with a molar concentration of 0.4 mol/L respectively;

S4: impregnating the acid-treated molecular sieve with the nickel chloride aqueous solution, enabling the mass ratio of adsorbed nickel ions to the heat-treated molecular sieve of Step 1 to be (0.05 to 0.08) to 1, and then completely drying to obtain a nickel ion supported molecular sieve; and S5: impregnating the nickel ion supported molecular sieve with the lanthanum trifluoromethanesulfonate aqueous solution until the molar ratio of the adsorbed lanthanum ions to the adsorbed nickel ions in step S4 is (1.5 to 2.5) to 1, and then completely drying again to obtain the solid supported catalyst.

2. The synthetic method according to claim 1, characterized in that the mass ratio of the adsorbed nickel ions to the heat-treated molecular sieve obtained in step S1 is (0.05 to 0.08) to 1 in step S4.

3. The synthetic method according to claim 1, characterized in that the molar ratio of the adsorbed lanthanum ions to the adsorbed nickel ions in step S4 is (1.5 to 2.5) to 1, most preferably 2 to 1 in step 55.

4. A solid supported catalyst according to claim 1.

5. A solid supported catalyst according to claim 2.

* * * * *